United States Patent [19]  [11]  4,311,665
Wu  [45]  Jan. 19, 1982

[54] SEPARATION AND ISOLATION OF CONJUGATED AND UNCONJUGATED BILIRUBIN

[75] Inventor: Tai-Wing Wu, Rochester, N.Y.

[73] Assignee: Eastman Kodak Company, Rochester, N.Y.

[21] Appl. No.: 101,663

[22] Filed: Dec. 10, 1979

Related U.S. Application Data

[63] Continuation-in-part of Ser. No. 56,585, Jul. 11, 1979, abandoned.

[51] Int. Cl.$^3$ .................. C07D 207/00; G01N 33/72
[52] U.S. Cl. .................................... 422/56; 23/230 B; 23/905; 252/408; 260/112 B; 542/434
[58] Field of Search ............................. 23/230 B, 905; 422/55-57; 260/112 B, 112 R, 314; 542/434; 252/408

[56] References Cited

U.S. PATENT DOCUMENTS 4,069,017  1/1978  Wu et al. .......................... 23/230 B

OTHER PUBLICATIONS

Abstract of Wu et al., "Human Conjugated Bilirubin--Isolation, Biosynthesis, & Molecular Characterization by Direct Spectroscopic Analyses" presented at the American Association for Clinical Chemistry 31st Annual Meeting in New Orleans, Louisiana, Jul. 15-20, 1979, Abstract appears in *Clinical Chemistry*, vol. 25, No. 6, p. 1137, (Jun. 1979).

J. Lucassen Doctoral Thesis, University of Utrecht, Netherlands, (1961).
With, *Bile Pigments*, Academic Press, New York, pp. 369-375, (1968).
Carey et al., "Self-Association of Unconjugated Bilirubin-Ix in Aqueous Solution at pH 10.0 and Physical-Chemical Interactions with Bile Salt Monomers and Micelles", Biochem. J. (1979), 179, 675-687.
Ostrow et al., Biochem. J. (1970), 120, 311-327.

*Primary Examiner*—Arnold Turk
*Attorney, Agent, or Firm*—J. Jeffrey Hawley

[57] ABSTRACT

A method is described for the separation and isolation of conjugated and unconjugated bilirubin from an aqueous liquid containing one or both of the bilirubin components. The aqueous liquid is contacted together with an interactive mordant for bilirubin to mordant bilirubin, the mordanted bilirubin is separated from the aqueous liquid, and the mordanted bilirubin is treated in an aqueous medium with a chaotropic agent at least slightly soluble in the medium to release the conjugated and/or unconjugated bilirubin from the mordant. A preferred embodiment also provides for selectively separating conjugated bilirubin from unconjugated bilirubin by selectively solubilizing either the conjugated or unconjugated bilirubin released from the mordant. Isolated conjugated bilirubin is thereby obtained having a purity in excess of 75%. A reference composition comprising the isolated conjugated bilirubin is also disclosed.

21 Claims, No Drawings

SEPARATION AND ISOLATION OF CONJUGATED AND UNCONJUGATED BILIRUBIN

This application is a continuation-in-part of Wu, U.S. patent application Ser. No. 056,585 filed July 11, 1979, now abandoned.

FIELD OF THE INVENTION

The present invention relates to a method for the separation and isolation of conjugated and unconjugated bilirubin from aqueous liquids, particularly liquids containing mixtures of conjugated and unconjugated bilirubin. The method is especially useful for the isolation of conjugated bilirubin from biological liquids such as serum.

BACKGROUND OF THE INVENTION

For over two decades, it has been generally assumed by clinical chemists that conjugated bilirubin ($B_c$) in humans is chiefly a diglucuronide and that $B_c$ exists in the same molecular form in a variety of different body fluids which contain this metabolic product, for example, serum, bile, and the like. Owing to the unstable nature of $B_c$, however, isolation of $B_c$ and specific molecular characterization of $B_c$ have been extremely difficult.

Definitive molecular characterization of $B_c$ has, to the knowledge of this inventor, been carried out for the first time by this inventor. See paper entitled "Human Conjugated Bilirubin—Isolation, Biosynthesis, and Molecular Characterization by Direct Spectroscopic Analyses" presented by T. W. Wu et al at the American Association for Clinical Chemistry 31th Annual Meeting in New Orleans, Louisiana, July 15–20, 1979. An abstract of this paper appears in *Clinical Chemistry*, Vol. 25, No. 6, p. 1137 (June, 1979). To determine the molecular structure of $B_c$, $B_c$ was isolated by the bile extraction and isolation procedure reported by Lucassen, J., doctoral thesis, University of Utrecht, Netherlands (1961). Bile was chosen for the separation and isolation of $B_c$ because of the high concentration of $B_c$ which exists in bile. The principal molecular species of $B_c$ isolated from bile by the Lucassen procedure has now been found not to be a diglucuronide as many have previously speculated, but rather a diester having a molecular weight of 918.2 and containing one molecule of glucuronic acid and one of glucuronolactone as shown in Formula I:

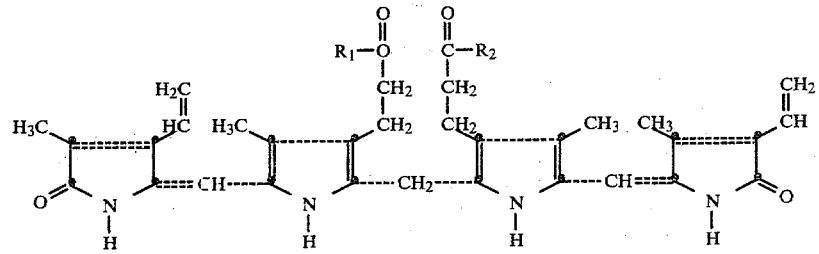

where
$R_1$ = glucuronic acid and $R_2$ = glucuronolactone or
$R_1$ = glucuronolactone and $R_2$ = glucuronic acid Recent work in the medical diagnostic field has indicated that the presence and concentration of $B_c$ in body fluids is of diagnostic significance, particularly in dealing with the treatment of certain jaundice conditions, e.g., in obstructive jaundice the small amount of $B_c$ normally present in adult human serum becomes elevated to form a larger proportion of the total bilirubin content thereof. The total bilirubin content consists of the sum of $B_c$ and the more familiar, predominant form of bilirubin referred to as unconjugated bilirubin ($B_u$).

To develop assay methods for bilirubin which selectively detect both $B_c$ and $B_u$, it became apparent that improved methods for separating and isolating $B_c$ and/or $B_u$ from aqueous liquids, particularly those containing mixtures of both $B_c$ and $B_u$, are necessary. This is because of the need to have $B_c$ and $B_u$ standards effective to calibrate assays for $B_c$ and $B_u$. At the present time, $B_u$ standards that can be purchased typically come from nonhuman bile sources, e.g., cow or ox, while $B_c$ standards are not available from either human or nonhuman animal sources. Various artificial standards have been used for bilirubin such as ferric thiocyanate, cobalt sulfate, potassium permanganate and the like. However, as reported by Winkelman, J. et al, *Clinical Chemistry—Principles and Technics*, R. J. Henry, D. C. Cannon, and J. W. Winkelman, Eds., Harper & Row Publishers, New York, 2nd Ed., 1974, pp 1038–1070, these artificial standards do not work well in spectrophotometric assays, because their absorption curves are not the same as that of bilirubin.

Although one could attempt to obtain a $B_c$ standard by use of the above-referenced Lucassen procedure, this procedure is difficult to perform. In addition, the Lucassen procedure provides little or no stabilization of $B_c$ during the isolation and extraction process, and therefore the $B_c$ has a pronounced tendency to degrade during the process. Moreover, the Lucassen procedure, although useful on bile which contains relatively high concentrations of $B_c$ and low concentrations of protein to which bilirubin readily binds, has never to the knowledge of the inventor been successfully applied to other aqueous biological liquids. For example, the Lucassen procedure has been found unsuccessful when applied to serum which contains relatively low amounts of $B_c$ and high concentrations of protein. Accordingly, a new method for separating and isolating $B_c$ and/or $B_u$ from bile as well as other aqueous liquids such as serum would be highly desirable.

Once separated and isolated, $B_c$ and/or $B_u$ can be employed for numerous clinical purposes such as in the manufacture and preparation of various standards, i.e., reference compositions, such as calibrators and controls, used in the assay of bilirubin contained in biological fluids such as serum, urine, cerebrospinal fluid, bile and the like.

SUMMARY OF THE INVENTION

The present invention provides a new method for the separation of conjugated and unconjugated bilirubin from aqueous liquids containing bilirubin. The method is particularly useful for the separation and isolation of conjugated bilirubin ($B_c$) and unconjugated bilirubin ($B_u$) from an aqueous liquid containing a mixture of $B_c$ and $B_u$. The method features the use of an interactive mordant for bilirubin having binding sites for bilirubin, the mordant comprising at least one moiety having a hydrophobic organic matrix containing a charge-bearing cationic group. The method comprises (a) contacting together an aqueous liquid containing $B_c$, $B_u$, or a mixture of $B_c$ and $B_u$ and the interactive mordant to mordant $B_c$, $B_u$, or the mixture of $B_c$ and $B_u$;

(b) separating the mordanted $B_c$ and/or $B_u$ of step (a) from the aqueous liquid; and (c) treating the mordanted $B_c$ and/or $B_u$ of step (b) in an aqueous medium with a chaotropic agent at least slightly soluble in the aqueous medium to release $B_c$ and/or $B_u$ from the mordant.

At the completion of step (c) noted above, $B_c$ and $B_u$ present in the original aqueous liquid have been separated from the liquid by the mordant and have been released from the mordant. The total bilirubin released in step (c), that is, the sum of the released $B_c$ and released $B_u$ in step (c), can then be used for whatever purpose desired, such as a component of a reference composition, for example, a component of a control fluid.

In accord with certain preferred embodiments of the present method, the chaotropic agent employed in step (c) is selected from the group consisting of ionizable salts; xanthine and alkylated xanthines, e.g., caffeine; non-ionic surfactants such as alkarylpolyethers; urea; and mixtures of the foregoing materials. Especially preferred chaotropic agents include ionizable salts; mixtures of sodium benzoate and an alkylated xanthine; and non-ionic surfactants.

In accord with an especially preferred embodiment of the present method, $B_c$ and $B_u$ are also selectively separated from one another. This is achieved in accord with the present method during or after step (c) by selectively solubilizing the released $B_c$ or released $B_u$. For example, in one embodiment, step (c) of the present method is carried out at a pH effective to solubilize the $B_c$ in the aqueous medium while the $B_u$ forms an insoluble solid phase in the aqueous medium. Accordingly, this embodiment effectively isolates $B_c$ from $B_u$, thereby permitting the selective isolation of these two bilirubin components. In another aspect of this embodiment, the selective separation of $B_c$ from $B_u$ can be achieved or further enhanced by addition of a water-miscible organic solvent following step (b) effective to aid selective solubilization of $B_c$. For example, propanol and other alkyl alcohols partially solubilize $B_c$ while $B_u$ is substantially insoluble in these alcohols. In yet another aspect of this embodiment, the released $B_u$ is separated from the released $B_c$ by extraction in a water-immiscible organic solvent in which $B_u$ is selectively solubilized, e.g., chloroform and dichloromethane.

A further embodiment of the invention provides isolated $B_c$ having a purity of from 75 to 90%, preferably in excess of 85% as determined by quantitative NMR (nuclear magnetic resonance) and gravimetric analysis. A reference composition comprising the isolated $B_c$ for assay of bilirubin contained in an aqueous liquid is also provided. This reference composition comprises a wet or dry matrix and the isolated $B_c$. In the case of a reference composition comprising a dry matrix, upon addition of an aqueous liquid, the resultant aqueous composition represents a useful reference fluid for calibrating clinical elements and reagents intended for assay of bilirubin in biological liquids, particularly quantitative assays of $B_c$ and total bilirubin, i.e., the sum of $B_c$ and $B_u$ contained in an aqueous liquid.

DESCRIPTION OF THE PREFERRED EMBODIMENTS

The present invention provides a new method for the separation and isolation of conjugated bilirubin ($B_c$) and/or unconjugated bilirubin ($B_u$) from aqueous liquids containing mixtures of $B_u$ and $B_c$. The method, of course, is also applicable to aqueous liquids in which the entire bilirubin content is composed solely of either $B_c$ or $B_u$. Because of the difficulty in distinguishing between the $B_c$ and $B_u$ components present in aqueous liquids containing mixtures of these components, and because $B_c$ is typically present in much lower concentration than $B_u$ and is also highly unstable and otherwise difficult to isolate, the method of the invention is particularly useful in the isolation of $B_c$ from aqueous liquids containing mixtures of $B_c$ and $B_u$.

The method of the invention will advantageously isolated $B_c$ and/or $B_u$ from a variety of aqueous liquids. For example, the method is applicable to aqueous biological liquids such as bile, serum, cerebrospinal fluid, urine, and the like derived from both human and nonhuman animal sources. In particular, the method is applicable to aqueous liquids, such as serum, even though these liquids contain relatively low amounts of $B_c$ and relatively large amounts of protein to which bilirubin is known to bind. A further advantage of the present method is that the interactive mordants used in the method appear to aid in stabilizing $B_c$ during the separation and isolation procedure of the method so that there is less tendency for degradation of the $B_c$ to occur.

The environmental conditions, including the temperature as well as the atmosphere under which the present method is carried out, can vary considerably. However, because of the susceptibility of bilirubin to degradation in oxidizing atmospheres and the general instability of bilirubin, particularly $B_c$, the method is preferably carried out in a non-oxidizing atmosphere, such as under nitrogen or an inert gas such as argon. Likewise, the temperature is preferably maintained within a range effective to avoid degradation of bilirubin, typically within a range of from about 0° to about 60° C., preferably from about 0° to about 10° C. By using the foregoing preferred conditions, one can optimize the amounts of $B_c$ and $B_u$ isolated.

To further optimize the amounts of $B_c$ and $B_u$ isolated, the present method is preferably carried out in the dark or under yellow safe-light conditions to avoid light-induced degradation of bilirubin.

In step (a) of the present method, the liquid containing a quantity of $B_c$ or $B_u$ to be isolated, typically a mixture of both $B_c$ and $B_u$, is contacted with an interactive mordant to mordant both $B_c$ and $B_u$. Typically, this is carried out by admixing an aqueous liquid containing the mordant dissolved or suspended therein and the aqueous bilirubin-containing liquid. Alternatively, the mordant can be admixed directly in the aqueous bilirubin-containing liquid as a dry powder; or the aqueous bilirubin-containing liquid can be applied to an essentially dry zone, e.g., a layer, comprising the mordant, for example, the dry test element described in U.S. Pat. No. 4,069,017. In still another embodiment, the interactive mordant can be packed in a column and the aqueous liquid containing bilirubin can be passed through the column to effect contact with the mordant.

The quantity of mordant used in this first step will vary depending upon the particular mordant selected, its binding capacity for $B_c$ and $B_u$, and the particular means whereby this step is carried out, e.g., whether the mordant is contained in an aqueous liquid at the time of contact, is present as a dry zone of a dry test element, or is packed in a column. To optimize the amount of $B_c$ or $B_u$ isolated by the present invention, one preferably employs in step (a) of the method an amount of mordant in excess of the maximum amount of $B_c$ and $B_u$ thought to be present in the liquid to insure that as much bilirubin as possible is mordanted in this step. When the mordant is added as a dry powder to the aqueous bilirubin-containing liquid or where the mordant is first dissolved or suspended in an aqueous liquid and then added to the aqueous bilirubin-containing liquid, a useful amount of the preferred copolymer mordants described in greater detail hereinafter, is typically sufficient to provide a final amount of mordant in the bilirubin-containing liquid within the range of from about 0.007 to 10 g% based on the total weight of mordant and aqueous liquid.

A useful test for determining the amount of a particular interactive mordant to be contacted together with a particular bilirubin-containing aqueous liquid can readily be performed by monitoring the absorption maxima of the mordanted bilirubin. That is, mordanted bilirubin exhibits enhanced absorptivity because of the interaction of the mordant and bilirubin. The respective absorption maxima of mordanted $B_c$ and $B_u$ can vary somewhat depending upon the particular interactive mordant, but typically an absorption maximum of mordanted $B_c$ occurs at about 420–430 ±20 nm and a maximum for mordanted $B_u$ occurs at about 460 nm ±20 nm. Thus, by monitoring the absorption maxima of mordanted $B_u$ and $B_c$ as the aqueous liquid sample is contacted with increasing amounts of the mordant, the addition of the mordant can be terminated at the point at which the absorption maxima of mordanted $B_c$ and mordanted $B_u$ stop increasing.

The length of time for contacting together the bilirubin-containing liquid and the interactive mordant to mordant $B_c$ or $B_u$ varies, depending upon the concentration of bilirubin in the liquid, the amount of mordant present, the binding capacity of the mordant, and the degree of intermolecular contact between the mordant and the bilirubin. Typically a contact time within the range of from about 10 seconds to 10 minutes is effective, although shorter or longer contact times can also be used depending upon the particular circumstances.

The pH at which the bilirubin-contacting liquid and mordant are contacted together is variable over a relatively wide pH range. For example, the pH may range from about 2 to 10, $B_u$ being soluble in a pH range of from about 7.4 to 10 and $B_c$ being soluble over the entire range of from about 2 to 10. Typically, where the aqueous liquid from which bilirubin is to be isolated is serum, the pH of the first step is carried out essentially at the pH of the serum. Normal human serum typically has a pH of about 7.35±0.05.

The first step of contacting together the aqueous, bilirubin-containing liquid and the mordant is preferably carried out under conditions under which the mordant is partially solubilized or readily suspended in aqueous liquid to insure good interaction between the mordant and bilirubin. In some cases, therefore, depending upon the particular mordant selected and its solubility in water, various organic liquid solubilizing agents for the mordant are added which are miscible with the aqueous bilirubin-containing liquid, for example, lower alkyl alcohols, lower alkyl ethers, and lower alkyl ketones, and the like containing 1 to about 3 carbon atoms in the alkyl group, for example, methanol. ethanol, tetrahydrofuran, acetone, and the like.

Having mordanted some and preferably most or all of the bilirubin present in the bilirubin-containing liquid, the mordanted bilirubin is separated from the aqueous liquid in step (b) of the present method. In the case where step (a) of the method is carried out essentially in a liquid medium, the step (b) separation step can readily be carried out by centrifugation. This is because of the low solubility of the mordanted bilirubin in aqueous liquids. However, other separation techniques including various filtration methods are also useful. Separation is preferably carried out at a temperature within the range of from about 0° C. to 10° C. Bilirubin is believed to be more stable at this reduced temperature and the solubility of the mordanted bilirubin at this reduced temperature may also be decreased, thereby facilitating the separation of the mordanted bilirubin from the aqueous liquid phase. Separation by centrifuging can conveniently be carried out at 15000×g for a time of about 5 to 15 minutes. However, other centrifuging conditions will also be useful. The aforementioned conditions are merely representative and are not to be regarded as critical.

In the case where step (a) of the present method is carried out by use of an essentially dry zone comprising the mordant, such as by use of the dry test element described in U.S. Pat. No. 4,069,017, the separation of the mordanted bilirubin from the aqueous liquid originally containing the bilirubin is readily carried out in accord with step (b) of the present method as follows: The aqueous liquid is allowed to penetrate into the mordant-containing zone of the element upon application of the liquid to the element in step (a), the bilirubin in the liquid binds to the mordant, and the mordanted bilirubin is then isolated from the dry mordant-containing zone of the element upon evaporation of the aqueous liquid.

Having separated the mordanted bilirubin in step (b) of the present method, the $B_c$ and $B_u$ are then released from the interactive mordant in step (c) of the method. To do this, the mordanted $B_c$ and $B_u$ are treated under appropriate pH conditions in an aqueous medium with a chaotropic agent at least slightly soluble in the aqueous medium. This treatment effects the release of bilirubin (both $B_c$ and $B_u$) from the mordant to which it is bound.

The chaotropic agent used in step (c) represents an at least slightly water-soluble, bond-disrupting material that disrupts the binding of the mordant with $B_u$ and/or $B_c$. The binding of the mordant to $B_u$ and $B_c$ is believed to occur through both ionic bonds and hydrophobic site bonds. A chaotropic agent effective to disrupt at least one of these bonding mechanisms, either the ionic or hydrophobic site bonds, is useful in the present method to release at least a portion of the $B_u$ and/or $B_c$ bound to the mordant.

One preferred chaotropic agent is a salt ionizable in the aqueous medium. The use of the salt to effect release of $B_c$ and $B_u$ from the mordant is believed to occur due to the reduction of the ionic binding capacity between the mordant and the bilirubin molecules in the presence of the soluble ions derived from the salt. A variety of salts are therefore known which can be used for this purpose. The salt should be at least slightly soluble in the aqueous medium and contain groups ionizable in the medium. The molecular size of the salt can be smaller, equal to, or greater than that of $B_c$ or $B_u$. Salts of strong acids and strong bases are preferred because of their ability to undergo essentially complete ionization and provide a large number of ions to the aqueous medium. In addition, for the same reason, i.e., the ability to undergo essentially complete ionization, the salts of strong acids and strong bases can readily be removed from the aqueous medium following release of $B_c$ and $B_u$. Because removal of the salt ions from the $B_c$- and $B_u$-containing aqueous medium is often desirable, choosing a salt of a strong acid and strong base becomes especially attractive. Sodium chloride has been found to work especially well as the ionizable salt. Other monovalent alkali metal and alkaline earth metal salts also represent preferred salts. However, a variety of other soluble, ionizable salts including polyvalent salts; ionic surfactants; and buffers, e.g., tris(hydroxymethyl)aminomethane hydrochloride, sodium citrate, and the like, can be used for this purpose. A partial listing of representative ionizable salts considered useful in the invention includes, in addition to sodium chloride, the following: potassium chloride, ammonium sulfate, cesium chloride, guanidinium hydrochloride, sodium benzoate, and the like.

The amount of salt employed to effect release of the bound bilirubin will depend, in large part, on the particular salt, its solubility, its degree of ionization in the aqueous medium selected, and the like. Typically, when employing salts of strong acids and strong bases such as sodium chloride, amounts of the salt effective to bring the molar concentration of the salt in the aqueous medium to a value within the range of from about 0.1 M to about 2 M have been found useful. However, for other types of salts, concentrations outside the aforementioned molarity values will also be useful.

Non-ionic surfactants at least slightly soluble in the aqueous medium of step (c) also represent a preferred class of chaotropic agent effective to release $B_c$ or $B_u$ from the mordant. The release of $B_u$ or $B_c$ from the interactive mordant in the presence of these non-ionic surfactants is theorized to occur as the non-ionic surfactant interferes with and thereby disrupts the hydrophobic bonding sites on the mordant for the $B_c$ or $B_u$. A partial listing of representative non-ionic surfactants can be found in McCutcheon's *Detergents and Emulsifiers*, 1974 North American Edition by the Allured Publishing Corporation. Specific, useful non-ionic surfactants include alkarylpolyethers, such as alkylphenoxypolyethoxyethanols having from 1 to about 9 carbon atoms in the alkyl group and 5 to about 40 ethoxy groups. These alkarylpolyethers are available from the Rohm and Haas Company under the tradenames Triton X-100, Triton X-102, Triton X305, Triton X-405, and the like. Other specific useful non-ionic surfactants are the polyoxyethylene sorbitan fatty acid esters such as polyoxyethylene sorbitan monolaurate sold under the tradename of Tween 20 by ICI America, Inc. Atlas Chemicals Division. The amount of the non-ionic surfactant useful in the present invention will vary, but typically an amount of non-ionic surfactant effective to bring the concentration of the surfactant in the aqueous medium to a value within about 0.1 to 10 g% have been found useful.

Other useful chaotropic agents include xanthine and xanthine homologs and derivatives, especially alkylated xanthines. Preferred alkylated xanthines include caffeine (1,3,7-trimethylxanthine), theobromine (3,7-dimethylxanthine), and theophylline (1,3-dimethylxanthine). One especially useful chaotropic agent comprises a mixture of xanthine and sodium benzoate, for example, a mixture of caffeine and sodium benzoate. The ratio of caffeine to sodium benzoate in the mixture is variable. Typically molar ratios of caffeine to sodium benzoate in the range of from about 1:2 to 1:10 are considered useful.

Yet another useful chaotropic agent is urea. As will be appreciated from the foregoing discussion, a variety of different chaotropic agents are useful in the present invention and the invention is not limited to a particular type or class of these agents. Furthermore, although useful chaotropic agents should be at least slightly soluble in an aqueous medium, good or even moderate solubility is not required. Xanthines, for example, are only slightly soluble in water. However, best results are generally obtained with chaotropic agents of moderate to excellent solubility in the aqueous medium. For purposes of the present specification, the phrase "slightly soluble" refers to a material having a solubility in water equal to or greater than that of xanthine (also known as 2,6-Purinedione).

At this point following completion of step (c), the $B_c$ and $B_u$ have effectively been separated from the other components of the original aqueous liquid by the interactive mordant and also released from the mordant. If desired, and in accord with an especially preferred embodiment of the present method, the $B_c$ and $B_u$ are also effectively separated from each other. This is achieved during or after step (c) of the method by selectively solubilizing $B_c$ or $B_u$. For example, in one embodiment, the mordanted $B_c$ and $B_u$ are treated with a chaotropic agent in step (c) at a pH which selectively solubilizes $B_c$ in an aqueous liquid phase supernatant while $B_u$ forms an insoluble solid phase. In this embodiment, which makes use of the aforementioned pH solubility characteristics of $B_c$ and $B_u$, step (c) is conducted at a pH less than 7.0, preferably 6.5 or lower, at which $B_c$ is soluble and $B_u$ is insoluble. In addition to the adjustment of pH conditions, a water-miscible organic solvent can be added following step (b), for example, during or after step (c), to separate or enhance separation of $B_c$ from $B_u$. For example, $B_c$ is soluble in propanol and propanol-water mixtures as well as in other water-miscible organic solvents such as alkyl alcohols having 1 to about 10 carbon atoms in the alkyl group thereof and mixtures of these solvents with water. $B_u$, on the other hand, remains substantially insoluble in aqueous alkyl alcohol mixtures, especially if the pH is maintained less than about 7.0.

Selective solubilization of $B_u$ or $B_c$ to permit separation and isolation of these two related bilirubin components from one another can also be achieved by organic solvent extraction of $B_u$ from $B_c$. This is, $B_u$ is more soluble than $B_c$ in water-immiscible organic solvents such as chloroform, dichloromethane, and the like. Thus, by extracting the released $B_u$ and $B_c$ from step (c) in such water-immiscible organic solvents, one selectively solubilizes $B_u$ and preferentially removes it from a mixture of $B_u$ and $B_c$.

In the preferred embodiment of the present method wherein $B_c$ is selectively isolated from $B_u$ during or following step (c) by appropriate adjustment of pH, the $B_c$ is solubilized in an aqueous liquid supernatant, and the $B_u$ is retained in a solid phase. The $B_c$-containing supernatant is readily isolated from the $B_u$-containing solid phase by centrifuging, decanting, filtering or the like. Thereafter, if desired, the liquid is partially or wholly removed from the supernatant such as by lyophilization (freeze-drying) to yield either a more concentrated aqueous solution of $B_c$ or a finely-divided powder containing $B_c$ together with the chaotropic agent and other impurities. Preferably, the liquid of the $B_c$-containing supernatant is only partially removed, and the resultant concentrated aqueous solution of $B_c$ is further treated to remove the chaotropic agent, thereby further purifying the $B_c$. For example, removal of a soluble, ionizable salt is carried out by any one of a number of conventional separation techniques including, but not limited to, ultrafiltration, dialysis, and chromatographic techniques such as thin-layer chromatography and column chromatography. Column chromatography, particularly molecular sieve column chromatography employing gel beads, such as LH-20 gel beads (LH-20 is a tradename of certain gel beads available from Pharmacia, Uppsala, Sweden), as the stationary phase and a lower alkyl alcohol-water mixture as the eluting medium, has been found especially useful.

Following these optional purification steps, aqueous media containing concentrated $B_c$, $B_u$, or mixtures of $B_c$ and $B_u$ can be stored, preferably in the dark or under yellow safelight conditions at low temperatures such as −75° C. to 10° C. under a vacuum or other non-oxidizing atmosphere to prevent degradation of the $B_c$. Preferably, the purified aqueous media containing concentrated $B_c$, $B_u$, or mixtures of $B_c$ and $B_u$ are freeze-dried to powder form for ease of storage. When needed, the dry powder is readily reconstituted by addition of aqueous liquid.

An especially useful embodiment of the present invention is the highly pure, isolated $B_c$ which is obtained. To the knowledge of the present inventor isolated $B_c$ with this degree of purity has heretofore never been obtained. In accord with the present invention, isolated $B_c$ having a purity in excess of 75%, preferably 85% to 90% or higher, as determined by quantitative NMR and gravimetric analysis is obtained.

A further embodiment of the invention provides reference compositions containing isolated $B_c$ useful as calibrators and controls for assays of aqueous liquids containing $B_c$. A major advantage of the reference compositions of the present invention is that the isolated conjugated bilirubin contained therein is not only of high purity, but also is substantially free of bile acids and other substances (such as hemoglobin) which can interfere with bilirubin assays. These reference compositions typically contain a wet or dry matrix and the desired amount of isolated $B_c$. If desired, a buffer, e.g., a phosphate buffer, is also present. In the case of a reference composition for assay of $B_c$ in serum, a typical reference composition comprises isolated $B_c$ and a serum matrix derived, for example, from pooled human serum or other aqueous medium that, under the conditions of the desired assay, behaves as serum does. Of course, the $B_c$ can be combined with matrices of other aqueous liquids for the assay of liquids other than serum, such as urine, cerebrospinal fluid, bile, and the like matrices. The concentration of the $B_c$ in such reference compositions will vary widely depending on the liquid to be assayed. Typical concentration ranges for the $B_c$ content of reference compositions useful for the assay of biological liquids extend from about 0.1 to 40 mg/dl.

To improve and optimize the yield of $B_c$ separated and isolated in accord with that embodiment of the present method wherein step (c) is carried out at a pH effective to solubilize $B_c$ while $B_u$ remains insoluble, one repeats step (c). That is, after treating the mordanted bilirubin in the presence of an aqueous medium at a pH of less than 7.0 with a chaotropic agent to release $B_c$ and $B_u$ and solubilize $B_c$ in the aqueous liquid supernatant, one separates the aqueous supernatant from the solid phase, retains the supernatant, and then subjects the solid phase to one or more additional treatments at a pH less than 7.0 to remove any additional $B_c$ that is present in the solid phase. Thereafter, each of the aqueous phase supernatants containing $B_c$ are collected and combined to form a single solution of $B_c$.

In accord with a further embodiment of the present method wherein $B_c$ is separated from $B_u$, the treatment of the mordanted bilirubin with the chaotropic agent in step (c) is carried out not only at a pH of less than 7.0 but also in the presence of an aqueous medium containing a volatile, water-miscible organic solvent. The presence of this volatile solvent is particularly useful because, among other reasons, it expedites any subsequent liquid removal step which is carried out to further concentrate and purify $B_c$. Typical of such volatile, water-miscible organic solvents are the alkyl alcohols having 1 to 10 carbon atoms in the alkyl group and the like. When such volatile solvents are employed, care should be taken to avoid those solvents which will also solubilize the $B_u$. In this regard, the alcohols such as octanol, propanol and the like are considered especially effective.

Other optional additives such as antioxidants, for example, sodium thiosulfite or ascorbic acid, can be employed during the present method to aid in preventing or retarding the oxidation or other forms of chemical or physical degradation of bilirubin, especially $B_c$.

The interactive mordants employed in the present method correspond to the mordants for bilirubin described in the aforementioned U.S. Pat. No. 4,069,017. In general, these mordants have multiple binding sites for bilirubin and contain at least one moiety having a hydrophobic organic matrix containing a charge-bearing cationic group. Such mordants are monomeric or polymeric, with especially preferred embodiments of such mordants represented by homopolymers or copolymers containing as a repeating unit a unit having a charge-bearing cationic group in a hydrophobic organic matrix. Materials having these properties and compositions bind both $B_c$ and $B_u$ and therefore these materials function as mordants for these bilirubin components. Not only do these materials act as mordants for these bilirubin components, but, in addition, bilirubin components mordanted by the binding sites of such interactive mordants produce mordanted bilirubin components exhibiting a significant increase in molar extinction coefficient and stability as compared to the unmordanted components. The charge-bearing cationic group present in the mordant typically retains its cationic charge in an aqueous environment regardless of pH fluctuation in the aqueous environment. The charge properties of the cationic group in the interactive mordant are therefore insensitive to pH.

Especially preferred polymeric interactive mordants have in the polymer chain, monomeric units of Formula II below:

II.

wherein

A represents an organo group and constitutes a portion of a polymer backbone;

Q represents a chemical bond(s) or a chemical group linking M⊕ to A;

M⊕ represents a hydrophobic organic moiety containing a cation, preferably a quaternary ammonium or phosphonium group; and X⊖ represents an acid anion such as a halide ion, for example, chloride or bromide; nitrate; methosulfate; p-toluenesulfonate; or an equivalent anion.

In certain especially useful embodiments, M⊕ represents a quaternary ammonium or phosphonium group having Formulas III or IV below:

$$R^1-\overset{|}{\underset{|}{N^\oplus}}-R^2$$
$$R^3$$

III.

$$R^1-\overset{|}{\underset{|}{P^\oplus}}-R^2$$
$$R^3$$

IV.

wherein each of $R^1$, $R^2$, and $R^3$, which are the same or different, represent an aryl, an aralkyl, or an alkaryl group having from about 5 to 20 carbon atoms or an alkyl group having from 1 to about 10 carbon atoms, preferably 4 to about 10 carbon atoms.

Preferably, Q, in Formula II represents a hydrocarbon group, preferably an arylene, arylenealkylene, alkylenearylene, arylenebisalkylene, or alkylenebisarylene group. Typically, although not required, Q contains from about 5 to 10 carbon atoms.

As will be appreciated, A in Formula II above can vary depending upon the particular polymeric backbone selected for use. Especially good results, however, have been obtained when A represents an alkylene group. Typically, such alkylene groups contain from about 2 to 10 carbon atoms.

Copolymers particularly useful as interactive mordants include copolymers containing about 10 to 90wt% of repeating units having Formula II hereinabove, and up to about 75 weight percent of additional repeating units comprising the residue of non-interfering monomers. The term "non-interfering repeating units" is used herein to include chemical units which do not chemically or physically interfere with the above-described mordanting of bilirubin. Monomer precursors which provide such non-interfering repeating units and which also impart hydrophobicity to the resultant mordant copolymer include addition-polymerizable aliphatic and aromatic hydrocarbons, such as olefins, substituted olefins, styrene, and substituted styrenes; alkylacrylates and methacrylates and derivatives thereof; and known equivalents for such monomer precursors. In addition, if desired, difunctional crosslinking groups are introduced into such copolymers to provide crosslinked copolymers useful as interactive mordants within the scope of the present invention.

The preferred polymeric interactive mordants described above have been found to exhibit even greater binding affinity for bilirubin than endogenous serum proteins such as albumin and ligandin.

The preferred polymeric interactive mordants used in the present method are only partially soluble in water. Therefore, these mordants are readily separated from aqueous mixtures thereof by various means such as centrifugation, filtration, and the like.

A partial listing of individual representative interactive mordants useful in the method of the invention include the following materials:

TABLE I

| Name | Structure |
|---|---|
| 1. Poly(N,N,N-trimethyl-N-vinyl-benzylammonium chloride) | 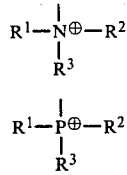 |
| 2. Poly[styrene-co-benzyl-(dimethyl)-p-vinyl-benzyl-ammonium chloride] | 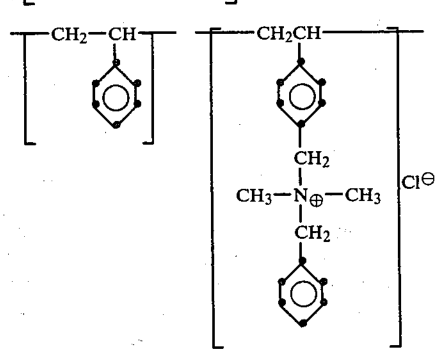 |

TABLE I-continued

| Name | Structure |
|---|---|
| 3. Poly(N,N,N-trioctyl-N-vinyl-benzylphosphonium chloride) | [structure: polymer with vinylbenzyl group bearing $-CH_2-P^{\oplus}(C_8H_{17})_3$ $Cl^{\ominus}$] |
| 4. Poly[styrene-co-(vinylbenzyl)-(trihexyl)-ammonium chloride] | [copolymer of styrene and vinylbenzyl-$N^{\oplus}(C_6H_{13})_3$ $Cl^{\ominus}$] |
| 5. Poly(N,N,N-trimethyl-N-vinylbenzylammonium chloride-co-styrene) | [copolymer of styrene and vinylbenzyl-$N^{\oplus}(CH_3)_3$ $Cl^{\ominus}$] |
| 6. Poly(styrene-co-N-vinyl-benzyl-N-benzyl-N,N-dimethyl-ammonium chloride-co-divinylbenzene) | [terpolymer of styrene, vinylbenzyl-$N^{\oplus}(CH_3)_2$-$CH_2$-phenyl $Cl^{\ominus}$, and divinylbenzene] |

Further extended description of such interactive mordants including methods of preparing such mordants will be found by reference to U.S. Pat. No. 4,069,017.

The following examples are presented to further illustrate the invention. The materials and procedures noted below were used in the examples:

CHEMICALS

Unless otherwise specified, all chemicals used were reagent grade. Sodium thiosulfite, $Na_2S_2O_3$ and the dihydrate of oxalic acid were purchased from Matheson, Coleman and Bell Manufacturing Chemists, Norwood, Ohio 45212. The polymeric mordants noted as mordants 4 and 6 refer to the mordants of the same number listed in Table I. All other chemicals in the examples including unconjugated bilirubin (except where it is specially referred to as being isolated from an aqueous liquid) were obtained from Eastman Organic Chemicals, Eastman Kodak Co., Rochester, N.Y. 14650.

FILM ELEMENT

The dry test element referred to as a "film" or "bilirubin film" in Example 1 represents an integral multi-layer bilirubin test element as described in U.S. Pat. No. 4,069,017. The element is composed of a surface spreading layer for distributing an aqueous sample to an underlying reagent layer containing mordant 6 of Table I which, in turn, is coated on a transparent poly(ethylene terephthalate) film base. The structure and composition of this "film" is similar to that described in detail in Example 2 of U.S. Pat. No. 4,069,017, except that the reagent layer also contained 8.608 g/m² of deionized gelatin and 0.2 M bicine buffer to provide a layer having a pH of 8.0 when spotted with 10 microliters of serum and the spreading layer also contained 2.69 g/m² caffeine and 4.035 g/m² sodium benzoate.

SERUM SAMPLES

Sera from jaundiced adults were specially supplied by local hospitals. All contained, according to versions of the Jendrassik-Grof assay, (as described in With, T. K., in *Bile Pigments, Chemical, Biological And Clinical Aspects*; Academic Press, New York and London, pp 360–410, 1968) a minimum of 10 mg/dl total bilirubin ($B_T$), of which 50–80% appeared as "direct-reacting bilirubin", sometimes considered to represent a measure of $B_c$. The freshly delivered samples were kept frozen at $-25°$ C. and in the dark for less than a week, or were processed immediately upon arrival.

CENTRIFUGATIONS

All centrifugations in the examples were conducted at 0–4° C. in a Beckman JC-21 centrifuge (Beckman Instrument Co.), using a JA-20 rotor.

EXAMPLE 1

Film-Based Method

Serum pooled from 3–4 jaundiced patient samples (each about 1–2 ml) was kept in the dark, on ice, and under a steady stream of nitrogen. A disposable pipette was used to apply about 0.5–1 ml of the serum pool in broad streaks (with total area of 7.5–12 cm$^2$) over a sheet of bilirubin film as described above. As soon as the last trace of fluid had penetrated the surface of the spreading layer (where application was made), another application was repeated over the same area. This was repeated until the serum pool was exhausted. The wetting was conducted in subdued light and under a nitrogen stream. When the wetting was completed, the spreading layer was gently, but thoroughly, removed (this can be done with the edge of a microscope slide). The spreading layer was discarded. Next, the exposed mordant-containing reagent layer, which appeared yellowish, was similarly separated from the film base and collected into thick-walled 50-ml centrifuge tubes. 1.0 ml of n-propanol and 1.0 ml of 2 M freshly prepared sodium chloride were added consecutively to each tube. The tube was sealed under nitrogen, shaken vigorously for 30 seconds, and left to stand at room temperature for 1–2 hours in the dark. The solution was then centrifuged for 10 minutes at 15,000 rpm. the yellowish colored supernatant was gently pipetted off, leaving a faintly yellow-colored pellet. The pellet was washed with propanol-NaCl twice as before and the washings were combined with the supernatant. The supernatant still contained small amounts of proteins and mordant. 2 ml of a caffeine-sodium benzoate solution (0.1 M: 0.2 M, final concentrations) were added to it under nitrogen and the mixture was stirred for one minute. Then the solution was adjusted to pH 5.5 with 1% oxalic acid, whereupon the residual protein and $B_u$ were precipitated, leaving $B_c$ in solution. The acidified $B_c$ solution was centrifuged at 10,000 rpm for 10 minutes. The pH of the supernatant was then readjusted to pH 7.0 with NaOH, mixed with an equal volume of ice-chilled chloroform under nitrogen and shaken for 30 seconds. The whole mixture was centrifuged at 5,000×g for 15 minutes and the aqueous supernatant was pipetted off carefully. For some preparations, this was the final step and the aqueous extract containing $B_c$ was freeze-dried overnight. Other preparations were further purified by passing the aqueous extract through a column packed with LH-20 gel beads (Pharmacia, Uppsala, Sweden) and 95% ethanol diluted 1:1 (v/v) with 0.1 M potassium phosphate buffer, pH 7.0. The same solvent mixture served as the eluting medium. The eluted yellow fraction was immediately dried, first under nitrogen, then under vacuum to give a dark brownish powder of concentrated $B_c$. Further results from this Example are summarized in Example 3.

EXAMPLE 2

Solution-Based Method

The following method was found to be particularly suitable for extracting $B_c$ from jaundiced sera having a total bilirubin concentration equal to or in excess of 20 mg/dl, of which 70–80% appeared as "direct" bilirubin in Jendrassik-Grof assay. Several of these samples appeared lipemic as well.

First, a pool of serum having a high $B_c$ concentration was diluted 1 to 5 (v/v) with distilled water under nitrogen. This solution was carefully titrated with mordant 4 (made up to 1% fresh in water containing 5–10% methanol) until the absorbance at 425 nm stopped increasing. With mild excess of mordant 4, the absorbance at 425 nm decreased slightly. The titrated solution appeared turbid and was rapidly centrifuged for 15 minutes at 15,000 g at 0°–4° C. The yellowish mordanted pellet was gently resuspended in 3 volumes of 0.05 to 0.1 M potassium phosphate buffer, pH 7.0, to which 1% $Na_2S_2O_3$ had been added. A fresh solution of caffeine and sodium benzoate was added dropwise to the cloudy suspension until the final level of caffeine was approximately 0.1 M and that of benzoate 0.2 M. During this time, the solution was stirred vigorously under nitrogen and in a bath of ice. The solution was allowed to stand for ½ hour in the dark and cold (0°–4° C.), then centrifuged at 10,000 g for 15 minutes. The supernatant was saved. The pellet was washed at least twice with an equal volume of 0.1 M potassium phosphate buffer, pH 7.0, then three to four times with a 1:1 (v/v) mixture of 1 M NaCl and n-propanol. The washings were pooled with the supernatant from the preceding centrifugation, then stirred under nitrogen and in the dark for ½ hour. The solution was freeze-dried; the resultant powder was resuspended in a minimal amount of water and loaded on a column packed with LH-20 gel beads and 95% ethanol diluted 1:1 (v/v) with 0.1 M potassium phosphate buffer, pH 7.0. The same solvent mixture served as the eluting medium. The yellow eluted fractions were pooled, rechromatographed on a fresh column as before, and immediately freeze-dried. The resulting brownish-yellow powder contained concentrated $B_c$ having a purity of about 85% based on quantitative NMR and gravimetric analysis. Further results from this Example are summarized in Example 3.

EXAMPLE 3

Spectroscopic Analysis And Summary of Results

A direct spectroscopic analysis of the $B_c$-containing powder obtained in both Examples 1 and 2 above was made by use of quantitative nuclear magnetic resonance and desorption mass spectrometry. The results of these analyses appear to confirm that the powder obtained in each example contained $B_c$ having the structure noted as Formula I in the "Background of the Invention". In addition, the serum-isolated $B_c$ obtained by the procedures of Examples 1 and 2 above was compared to that isolated from bile using the Lucassen procedure referenced in the "Background of the Invention". The serum-isolated $B_c$ obtained by the procedures of Examples 1 and 2 was found to be very similar to that from bile in terms of physical appearance, solubility, hydroscopicity, lability to air and light, diazo reactivity, and chromatographic behavior.

The powdered $B_c$-containing isolates prepared by either Example 1 or 2 were kept in the dark, at −25° C., under vacuum and in a desiccated environment. Under these conditions of keeping, there was no discernible change in the visible spectral characteristics of the powdered $B_c$-containing isolates for periods up to two months. If exposed to air, moisture, or light, the powder readily turned green. When the $B_c$-containing powder was reconstituted with water in the presence of 2-4 g% human serum albumin, the $B_c$ appeared significantly more stable.

Further results from the procedures of Examples 1 and 2 to isolate $B_c$ are summarized in Table II. The data illustrate that regardless of the method, the nominal yields (expressed as mg "dry" weight per 10 ml of pooled serum) were highly comparable. The yields thus obtained appeared substantially higher than those reported to date in With, T.K., *Bile Pigments, Chemical, Biological and Clinical Aspects*, Academic Press, New York and London, 1968. This is attributed to the use of the mordants described herein which appear to be highly specific for $B_c$ and $B_u$ and to stabilize the otherwise highly labile $B_c$ during the isolation procedure.

purified by passing the total bilirubin in a liquid medium composed of a chloroform methanol-water mixture (95:35:6 v/v) through a column packed with LH-20 gel beads. $B_u$ and $B_c$ were then separately removed from the column. $B_u$ was removed by using dichloromethane as the eluting medium. Thereafter, $B_c$ was removed from the column using distilled water as the eluting medium. The two purified bilirubin components thus obtained were pooled and dried under nitrogen. The yield of total bilirubin obtained by this procedure, averaged over several repeats of the procedure on rabbit bile, ranged from 50-80%. The yield of total bilirubin obtained by this procedure, averaged over several repeats of the procedure on dog bile, ranged from 30 to 50%.

The invention has been described in detail with par-

TABLE II

Summary of Serum $B_c$ Isolation

| Isolation Procedure | | Example 1<br>Film-Based Method | Example 2<br>Solution-Based Method |
|---|---|---|---|
| Starting volume (ml) | | 5-8 ml (range of 3 separate pools) | 5-10 ml (range of 2 separate pools) |
| Type of sera pooled | | Mostly freshly drawn, with pH range 7.5-7.9 $B_T$>20 mg/dl and nominal $B_c$>50% $B_T$ | Mostly freshly delivered, some frozen ($-25°$ C.) for a few days before processing; $B_T \geqq 20$ mg/dl with >>50% $B_c$, pH range 7.38-8.15 included highly lipemic sera |
| Estimated total mg "$B_c$" in starting pools | | 2.2-3.0 | 1.8-3.5 |
| Yield (mg) - apparent dry weight** of isolate per ml of serum pool | | 0.83-0.98 (with LH-20 column step)<br>0.95-1.16 (without LH-20 step) | 0.42-1.55 |
| General physical characteristics | | Fluffy dark-brownish powder; hygroscopic; very water-soluble; turns green in moist air or in light | |
| Diazo reactivity | | Reacts instantaneously and positively with the diazo reagent,*** giving purplish-pink product even in absence of promotor (or alcohol) | |
| Thin-Layer Chromatography (TLC) | | Remains near origin of TLC plates (composed of silica gel G from Eastman Organic Chemicals when run in $CHCl_3:CH_3OH:H_2O$ (95:30:4, v/v) while authentic $B_u$ (Eastman Organic Chemicals) runs with distinctly higher mobility; mobility of serum $B_c$ isolate similar to bile $B_c$ isolate | |
| Chromatographic behavior | Gel filtration on LH-20 column packed in 95% ethanol | Elution position indicates molecular mass in the range of 900-1000 when judged against known molecular markers. However, the presence of even small amounts (e.g., 0.5g% human serum albumin) has been observed to significantly alter elution volume of the major fraction in serum isolates | |

**Since $B_c$ is very hygroscopic, this dry weight may be subject to some error.
***Manual Jendrassik-Grof assay as directed in Routh, J. I., Fundamentals of Clinical Chemistry N. W. Tietz, Ed., W. B. Saunders Co., Philadelphia, London, Toronto (1970) pp 743-762.

EXAMPLE 4

Extraction of $B_c$ and $B_u$ From Aqueous Liquids of Non-Human Origin

The method of the present invention can be used to separate both bilirubin components, i.e., $B_c$ and/or $B_u$, from aqueous mammalian liquids other than those of human origin. In this example, a modified "Solution-Based Method" similar to that of Example 2 above was employed to successfully separate $B_c$ and $B_u$ from both dog and rabbit bile. In this example, the procedure of Example 2 was modified as follows: Mordant No. 6 of Table I was used in place of Mordant No. 4 of Table I. The $B_c$ and $B_u$ extracted by the mordant were released from the mordant by washing the mordanted $B_c$ and $B_u$ with a 1% aqueous solution of the non-ionic surfactant octyl phenoxypolyethoxy ethanol, Triton X-100 a tradename of Rohm & Haas Co., having a pH of about 7-7.4 followed by washing with an aqueous caffeine-sodium benzoate solution having a pH of about 7.0 and containing a concentration of caffeine and sodium benzoate of 0.1 M and 0.2 M, respectively. The resultant washings were pooled and contained both $B_c$ and $B_u$ released from the mordant. The mixture of $B_c$ and $B_u$ thus obtained, i.e., the total bilirubin, was then further ticular reference to contain preferred embodiments thereof, but it will be understood that variations and modifications can be effected within the spirit and scope of the invention.

What is claimed is:

1. A method for the separation and isolation of conjugated bilirubin ($B_c$) and unconjugated bilirubin ($B_u$) from an aqueous liquid containing $B_c$, $B_u$, or a mixture of $B_c$ and $B_u$, said method comprising:

(a) contacting together said liquid and an interactive mordant having binding sites for bilirubin to mordant said $B_c$, $B_u$, or mixtures of $B_c$ and $B_u$, said mordant comprising at least one moiety having a hydrophobic organic matrix containing a charge-bearing cationic group;

(b) separating the mordanted $B_c$ and/or $B_u$ of step (a) from said liquid; and (c) treating the mordanted $B_c$ and/or $B_u$ of step (b) in an aqueous medium with a chaotropic agent at least slightly soluble in said medium to release $B_c$ and/or $B_u$ from said mordant.

2. A method as defined in claim 1 wherein said chaotropic agent in step (c) is selected from the group consisting of ionizable salts, non-ionic surfactants, xanthine and alkylated xanthines, urea, and mixtures thereof.

3. A method as defined in claim 1 or 2 wherein said interactive mordant is a polymeric mordant having monomeric units in the polymer chain of the following formula

wherein
- A represents an organo group constituting a portion of the polymer backbone;
- Q represents a chemical bond(s) or a chemical group linking $M^{\oplus}$ to A;
- $M^{\oplus}$ represents a hydrophobic organic moiety containing a cation; and
- $X^{\ominus}$ represents an acid anion.

4. A method for the selective separation and isolation of conjugated bilirubin ($B_c$) and unconjugated bilirubin ($B_u$) from an aqueous liquid containing a mixture of $B_c$ and $B_u$, said method comprising:
   (a) contacting together said liquid and an interactive mordant having binding sites for bilirubin to mordant said $B_c$ and $B_u$ in said liquid, said mordant comprising at least one moiety having a hydrophobic organic matrix containing a charge-bearing cationic group;
   (b) separating the mordanted $B_c$ and $B_u$ of step (a) from said liquid; and
   (c) treating the mordanted $B_c$ and $B_u$ of step (b) in an aqueous medium with a chaotropic agent at least slightly soluble in said medium to release $B_c$ and $B_u$ from the mordant; and
   (d) selectively solubilizing the released $B_c$ and $B_u$ of step (c) to separate $B_c$ from $B_u$.

5. A method of claim 4 wherein step (d) is carried out during or after step (c) by adjusting the pH of said aqueous medium to a value effective to solubilize the released $B_c$ in said medium while the released $B_u$ forms an insoluble solid phase in said medium.

6. A method of claim 1, 4 or 5 wherein a volatile water-miscible organic solvent is added to said mordanted $B_c$ and $B_u$ following step (b).

7. A method of claim 4 wherein step (d) is carried out by extraction in a water-immiscible organic solvent in which $B_u$ is selectively solubilized.

8. A method of claim 4 wherein step (d) is carried out by extraction in chloroform, dichloromethane, or mixtures thereof to selectively solubilize $B_u$ therein.

9. A method of claim 1 or 4 wherein said method is carried out at a temperature in the range of from about 0° to 10° C.

10. A method of claim 1 or 4 wherein said method is carried out in a non-oxidizing atmosphere.

11. A method of claim 1 or 4 wherein step (a) is carried out in a dry test element.

12. A method of claim 1 or 4 wherein step (a) is carried out by contacting together in an aqueous medium said interactive mordant and said liquid.

13. A method for the selective separation and isolation of conjugated bilirubin ($B_c$) and unconjugated bilirubin ($B_u$) from an aqueous liquid containing a mixture of $B_c$ and $B_u$, said method comprising:

(a) contacting together said liquid and an interactive mordant having binding sites for bilirubin to mordant said $B_c$ and $B_u$, said interactive mordant representing a polymeric mordant having monomeric units in the polymer chain of the following formula

wherein
- A represents an organo group constituting a portion of the polymer backbone,
- Q represents a chemical bond(s) or a chemical group linking $M^{\oplus}$ to A,
- $M^{\oplus}$ represents a hydrophobic organic moiety containing a cation, and
- $X^{\ominus}$ represents an acid anion;
   (b) separating the mordanted $B_c$ and $B_u$ of step (a) from said liquid;
   (c) treating the mordanted $B_c$ and $B_u$ of step (b) in an aqueous medium with a chaotropic agent at least slightly soluble in said medium to release $B_c$ and $B_u$ from the mordant, said chaotropic agent selected from the group consisting of ionizable salts, non-ionic surfactants, xanthine and alkylated xanthines, urea, and mixtures thereof; and
   (d) selectively solubilizing the released $B_c$ or $B_u$ of step (c) to separate $B_c$ from $B_u$.

14. A method of claim 13 wherein said interactive mordant is a copolymer containing about 10 to 90 wt% of repeating units having the formula specified in step (a) of claim 13 and up to about 75 wt% of repeating units of a noninterfering hydrophobic monomer.

15. A method of claim 13 wherein step (d) is carried out during step (c) by adjusting the pH of said aqueous medium to a value less than 7.0 whereby released $B_c$ is solubilized in said medium and released $B_u$ forms an insoluble solid phase in said medium.

16. A method of claim 13 or 15 wherein said chaotropic agent comprises a salt of a strong acid and a strong base and wherein a volatile, water-miscible organic solvent is added to said aqueous medium in step (c).

17. A method of claim 13 or 15 wherein said chaotropic agent comprises a salt of a strong acid and a strong base and wherein propanol is added to said aqueous medium in step (c).

18. A method of claim 13 wherein said method is carried out under a non-oxidizing atmosphere at a temperature within the range of from about 0° to 60° C.

19. Isolated conjugated bilirubin having a purity in excess of 75% as determined by quantitative nuclear magnetic resonance and gravimetric analysis.

20. Isolated conjugated bilirubin having a purity of about 85% or higher as determined by quantitative nuclear magnetic resonance and gravimetric analysis.

21. An article of manufacture for the assay of bilirubin contained in an aqueous liquid, said article comprising a wet or dry matrix, and isolated conjugated bilirubin having a purity of 75% or higher as determined by quantitative nuclear magnetic resonance and gravimetric analysis.

* * * * *